United States Patent
Salmon et al.

(10) Patent No.: US 10,751,499 B2
(45) Date of Patent: Aug. 25, 2020

(54) FLEXIBLE MASK COUPLING

(71) Applicant: Fisher & Paykel Healthcare Limited, Auckland (NZ)

(72) Inventors: Andrew Paul Maxwell Salmon, Auckland (NZ); Brett John Huddart, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 985 days.

(21) Appl. No.: 14/783,624

(22) PCT Filed: Apr. 4, 2014

(86) PCT No.: PCT/NZ2014/000057
§ 371 (c)(1),
(2) Date: Oct. 9, 2015

(87) PCT Pub. No.: WO2014/168489
PCT Pub. Date: Oct. 16, 2014

(65) Prior Publication Data
US 2016/0067442 A1 Mar. 10, 2016

Related U.S. Application Data

(60) Provisional application No. 61/811,017, filed on Apr. 11, 2013.

(51) Int. Cl.
*A61M 16/08* (2006.01)
*A61M 16/06* (2006.01)

(52) U.S. Cl.
CPC .... *A61M 16/0825* (2014.02); *A61M 16/0616* (2014.02); *A61M 16/0683* (2013.01); *A61M 16/0816* (2013.01)

(58) Field of Classification Search
CPC ............... A61M 16/06–0694; A61M 16/0825
See application file for complete search history.

(56) References Cited

U.S. PATENT DOCUMENTS

| | | | |
|---|---|---|---|
| 5,921,239 A * | 7/1999 | McCall | A61M 16/06 128/205.25 |
| 10,188,819 B2 | 1/2019 | Chodkowski et al. | |
| 2005/0076913 A1* | 4/2005 | Ho | A61M 16/06 128/206.27 |
| 2005/0150497 A1* | 7/2005 | Eifler | A61M 16/06 128/206.21 |

(Continued)

FOREIGN PATENT DOCUMENTS

| | | |
|---|---|---|
| CN | 101282767 A | 10/2008 |
| CN | 101479010 A | 7/2009 |

(Continued)

OTHER PUBLICATIONS

International Search Report; PCT/NZ2014/000057; dated Jul. 10, 2014; 3 pages.

(Continued)

*Primary Examiner* — Valerie L Woodward
(74) *Attorney, Agent, or Firm* — Knobbe, Martens, Olson & Bear, LLP

(57) ABSTRACT

Mask interfaces having mask frames and mask seals are disclosed. Headgear and breathing conduits can be connected to the mask interfaces. The connection between the mask seals and the mask frames can enable movement of the mask seals relative to the mask frames. The relative movement may be at the mounting locations of the mask seals and mask frames.

11 Claims, 4 Drawing Sheets

(56) References Cited

U.S. PATENT DOCUMENTS

| | | | |
|---|---|---|---|
| 2005/0155603 A1* | 7/2005 | Frerichs | A61M 16/06 128/206.21 |
| 2006/0283456 A1 | 12/2006 | Geiselhart et al. | |
| 2006/0283458 A1* | 12/2006 | Woodard | A61M 16/06 128/206.24 |
| 2007/0044804 A1* | 3/2007 | Matula, Jr. | A61M 16/06 128/206.21 |
| 2007/0209663 A1* | 9/2007 | Marque | A61M 16/0683 128/207.11 |
| 2008/0066745 A1* | 3/2008 | Janbakhsh | A61M 16/06 128/200.24 |
| 2008/0210241 A1* | 9/2008 | Schulz | A61M 16/06 128/206.21 |
| 2015/0297854 A1* | 10/2015 | McCracken | A61M 16/06 128/201.23 |
| 2017/0333657 A1* | 11/2017 | Stephenson | A61M 16/06 |

FOREIGN PATENT DOCUMENTS

| | | |
|---|---|---|
| WO | WO 2010/131189 | 11/2010 |
| WO | WO 2012/020359 | 2/2012 |
| WO | WO 2012/140514 | 10/2012 |

OTHER PUBLICATIONS

Written Opinion of the ISA; PCT/NZ2014/000057; dated Jul. 10, 2014; 4 pages.

European Search Report; PCT/NZ2014/000057; dated Nov. 23, 2016; 8 pages.

Republic of China Office Action with English Translation; dated Dec. 6, 2016; 20 pages.

Extended European Search Report for Application No. 19177029.6 dated Aug. 14, 2019 in 6 pages.

* cited by examiner

FLEXIBLE MASK COUPLING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosure generally relates to connections between mask frames and mask seals. More particularly, the present disclosure relates to such connections that facilitate relative movement between the mask frames and mask seals.

Description of the Related Art

The treatment of obstructive sleep apnea (OSA) by continuous positive airway pressure (CPAP) flow generator systems involves the continuous delivery of pressurized air to the airways of a human via a conduit and an interface (e.g., a mask). Typically, the interface creates at least a substantial "seal" on or around the nose and/or the mouth. This act of creating a "seal" results in pressurization of the patient's airway and the CPAP system.

Due to the simple physics of pressurising this mask, it results in a force being generated that is proportional to the projected area of the mask and the pressure difference between the inside and the outside of the mask. For the mask to be stable on the patient's face, this force must be opposed by an equal and opposite force. A head gear system is typically used to provide the equal and opposite force.

In addition to this direct force created by the pressurization of the mask, there are a number of external forces that the head gear also counteracts. Examples of other external forces includes pull or drag on the delivery tube and loading induced by the patient/bedding on the mask as the patent moves.

SUMMARY OF THE DISCLOSURE

These external forces typically are considerably larger (e.g., about 3-5 times larger) than the force required to restrain the mask against the pressure-based movement. The implications that this has on traditional mask and headgear system is that changes to the external forces typically result in movement of the mask system until the headgear system is able to counteract these forces.

The movement of the mask system results in loading change and/or movement of the seal, either of which can change how the seal interacts with the patient's skin. This change may be in the pressure level the seal exerts on the patient's skin or, in some cases, it is sufficient to enable a leak to be created between the seal and the patient's skin.

The effect of these changes on the patient is that the patient interacts with the mask system to reposition it on their face, in either a sub-conscious manner or a conscious manner, in order to correct the fit, which may be defined as an "equipment induced" sleep interruption. Equipment induced sleep interruption compromises the therapy that the patient is receiving.

The creation of practical and not so practical solutions to the underlying causes of equipment induced sleep interruption has been the subject of considerable development effort from numerous organizations, which has resulted in numerous patents.

The following is a description of a number of practical options to improve current designs by providing a decoupling mechanism between the mask seal member and the mask frame to minimise the effect on the seal of external forces exerted on the mask frame and/or small movement of the mask frame. In effect, certain features, aspects and advantages of various embodiments of the present disclosure provide a "suspension" mechanism between the seal and the mask frame.

An object of the present disclosure is to provide an interface that will at least provide the industry and users with useful choice.

In accordance with at least one of the embodiments disclosed herein, a patient interface is provided comprising a seal portion sized and shaped to surround the nose and/or mouth of a user and adapted to create at least a substantial seal with the user's face, a frame portion adapted to couple to the seal portion, a connector that permits the interface to be coupled to a conduit; and a coupling that permits the seal portion to move relative to the frame portion.

In some configurations, the relative movement of the seal portion is generally constrained to a slip plane across the frame portion of the interface. The relative movement can be permitted generally across and/or perpendicular to the slip plane.

In some configurations, the relative movement of the seal portion is constrained to a spherical boundary. The coupling can be a ball and socket type joint. The relative movement can be permitted around a common rotational center. In some configurations, the relative movement can be permitted along a principal axis of the ball and socket joint. The seal portion can comprise a socket and the frame portion can comprise a complementary ball.

In some configurations, the relative movement of the seal portion is constrained to a cylindrical boundary. The coupling can be a shaft and bearing type joint. The relative movement can be permitted along an axis of the cylindrical boundary.

In some configurations, the patient interface can comprise any combination of the relative movements described above.

In accordance with at least one of the embodiments disclosed herein, a patient interface is provided comprising a seal portion sized and shaped to surround the nose and/or mouth of a user and adapted to create at least a substantial seal with the user's face, the seal portion comprising a seal inlet; a frame portion comprising a frame inlet and a frame outlet, the frame portion adapted to couple to the seal portion; a connector comprising a first end adapted to couple with the frame inlet and a second end that permits the interface to be coupled to a conduit; and a coupling adapted to couple the frame outlet and the seal inlet, and permit the seal portion to move relative to the frame portion; wherein the coupling is generally the same size and generally aligned with the frame inlet.

In some configurations, the relative movement of the seal portion is generally constrained to a slip plane across the frame portion of the interface. The relative movement can be permitted generally across and/or perpendicular to the slip plane.

In some configurations, the coupling is made of a flexible material. The coupling can have a bellows construction.

The term "comprising" as used in the specification and claims means "consisting at least in part of". When interpreting a statement in this specification and claims that includes "comprising," features other than that or those prefaced by the term may also be present. Related terms, such as "comprise" and "comprises," are to be interpreted in the same manner.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present disclosure will now be described with reference to the drawings of one or more preferred embodiments, which embodiments are intended to illustrate and not to limit the disclosure, and in which figures.

DETAILED DESCRIPTION OF SPECIFIC EMBODIMENTS

Figure 4:
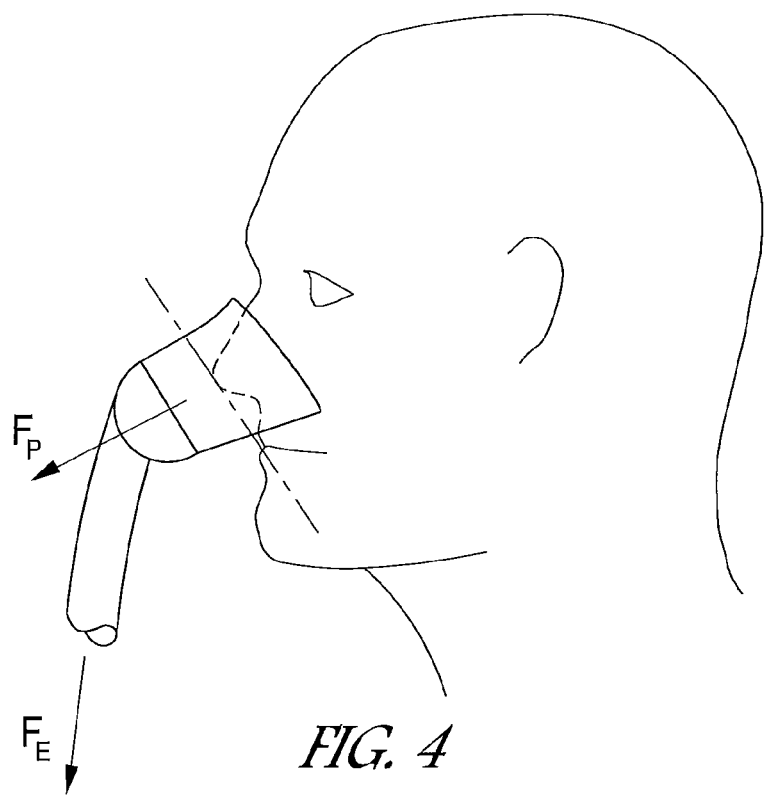
FIG. 4 shows a nasal mask and associated force vectors.
Figure 5A:
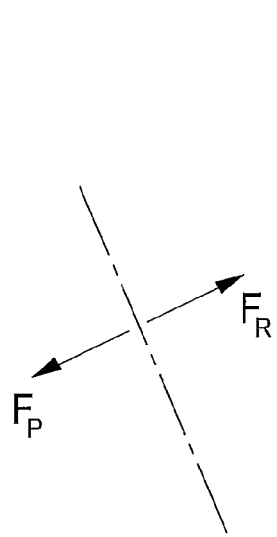
FIG. 5A shows the force vectors for a mask with no external forces.

The application of pressure to the inside of a mask results in a force vector being created which can be restrained by an equal and opposite force, as discussed above. FIG. 4 shows an example of such a configuration using a side view of a nasal mask wearer. The pressure force vector $F_P$ that results is a combination of the pressure difference between the inside and the outside of the mask seal, the projected area of the mask seal and the orientation of the mask. Over the combination of pressures potentially used for CPAP (about 4-20 cm water), for a typical nasal mask, this force varies between at least about 0.7N and less than or equal to about 3.5N. FIG. 5A illustrates the force vectors for situations with no external forces. As shown in the figure, the pressure force $F_P$ is restrained by an equal and opposite retention force $F_R$, which can be provided by headgear or other retention system.

Figure 5B:
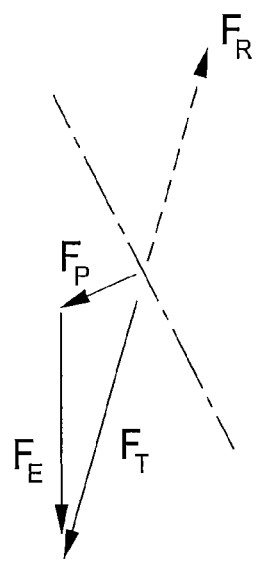
FIG. 5B shows the force vectors for a mask with external forces.

FIG. 4 also shows an external force $F_E$ that can be exerted on the mask, such as by pulling forces from an attached hose or other external forces. FIG. 5B illustrates the force vectors for situations that include external forces $F_E$. As shown in FIG. 5B, the combination of the pressure force $F_P$ and the external force $F_E$ can have a total force $F_T$. The total force $F_T$ is restrained by an equal and opposite retention force $F_R$, which can be provided by headgear or other retention system.

The external forces $F_E$ that may be applied to a mask system, primarily from hose drag, typically result in mask retention forces $F_R$ being about 3-5 times greater than what is required to purely hold the mask in place (e.g., at least about 10.5N to less than or equal to 17.5N). The vector that these external forces $F_E$ pass though varies due to the nature of how they are created and, to resolve them, a small amount of head gear stretch or slip may occur.

Because the force that opposes hose pull is considerably larger than the minimum force required to hold the seal in place, the hose pull-based force dominates and, when a conventional mask is in use, the hose pull-based force results in seal movement on the patients face, which typically creates a leak or compromises therapy.

Figure 1:
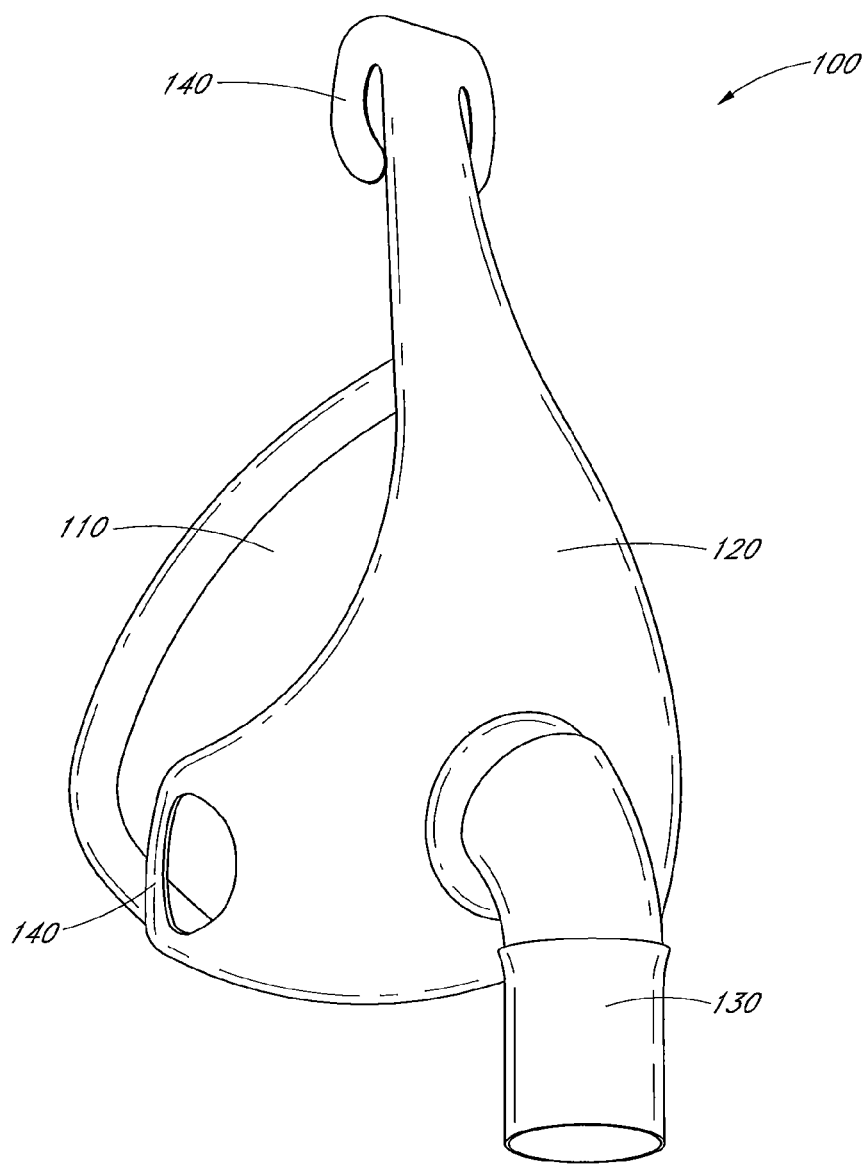
FIG. 1 shows the design of a typical mask.

With reference to FIG. 1, a mask interface 100 generally comprises a mask seal 110, which is configured to be positioned on the skin of a patient, and a frame 120, to which the mask seal is mounted. The mask frame 120 can include attachment points 140 for headgear or otherwise be configured to connect to headgear. A conduit can be connected to one or more of the mask frame and the mask seal. In some configurations, the connection to the mask frame and/or mask seal is a rotating connector or swiveling connector. In the illustrated configuration, the conduit can be connected to a ball jointed elbow 130 and the ball jointed elbow is connected to the mask frame 120.

Figure 2:
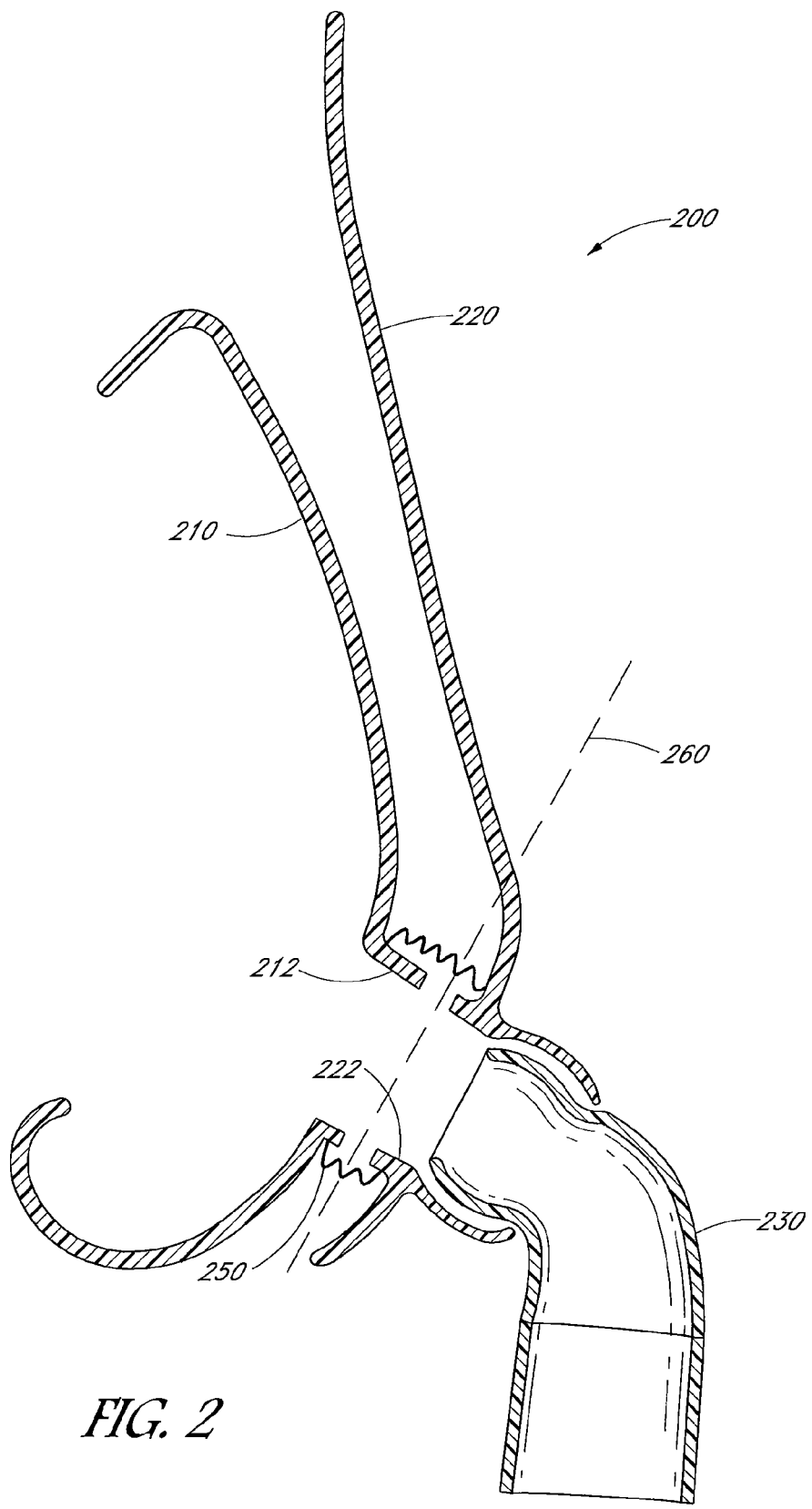
FIG. 2 shows a cross section through a mask with a flexible coupling between the mask seal and the mask frame.
Figure 3:
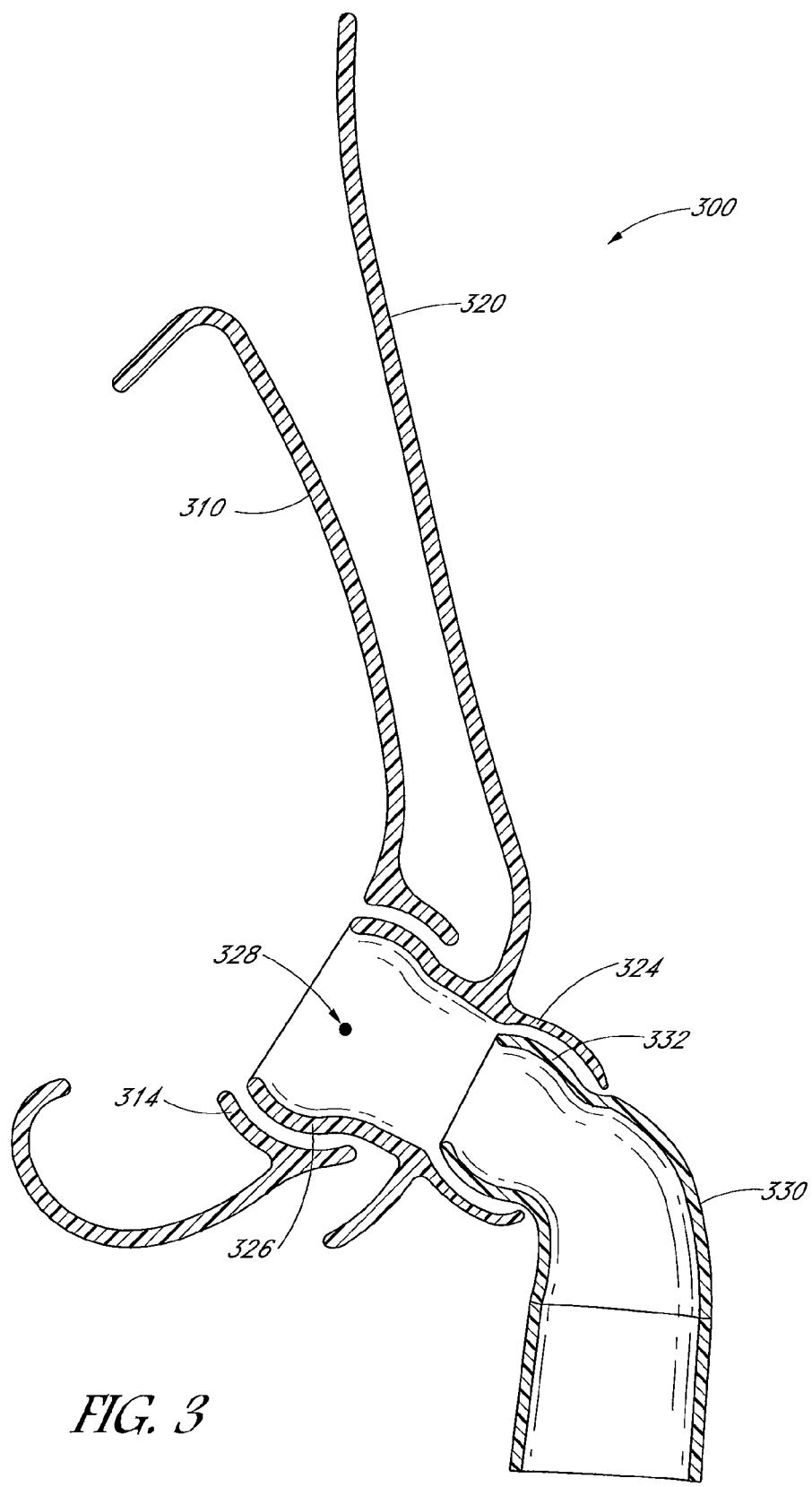
FIG. 3 shows a cross section through a mask with a ball and socket style coupling between the mask seal and the mask frame.

The disclosed mask assemblies seek to decouple or segregate the mask seal from the mask frame that carries/supports the tube connection. There are a number of embodiments to achieve the segregation. With reference to FIGS. 2-3, some embodiments of a mask interface in accordance with the present disclosure are illustrated.

In some configurations, such as the interface 200 shown in FIG. 2, the mask seal 210 includes a seal inlet 212 and the mask frame 220 includes a frame outlet 222. In the illustrated configuration, the seal inlet 212 and the frame outlet 222 are shown as male connectors. The seal inlet 212 and frame outlet 222 can be coupled by a coupling member 250, which can be flexible or otherwise allow relative movement between the mask seal 210 and mask frame 220. For example, the coupling member can at least partially be made of rubbers, textiles, plastics, or other suitable material and can be flexible and/or stretchable. In some configurations, the coupling member can be a slip coupling. In the illustrated configuration, the coupling member 250 comprises an articulable member. The articulable member can have a bellows construction with an undulating side wall.

With continued reference to FIG. 2, the interface 200 can have a connector 230 for connection with a conduit that is in fluid communication with a gas delivery system. The connector 230 can be configured to be coupled with a frame inlet of the mask frame 220. In the illustrated configuration, the connector 230 and mask frame 220 have a ball and socket connection. In other configurations, other connection types can be used, such as rotational couplings and fixed joints. The frame outlet 222 and the seal inlet 212 can be generally aligned with the frame inlet. The area of the opening of the seal inlet 212 and the frame outlet 222 can be approximately the same size as the opening of the frame inlet. This can allow the flow of gases to travel through the interface without substantially impeding, restricting or reducing the flowrate of the gases flow. The coupling member 250 can also be generally the same size and generally aligned with the frame inlet. This advantageously helps improve the flexibility and relative movement between the seal portion and frame portion. For example, because the coupling member is localized around the frame inlet, as opposed to a larger perimeter of the seal portion, the coupling member is more easily bendable and provides improved flexibility between the seal portion and the frame portion. In some configurations, the coupling member 250 can have non-uniform stiffness or structure to allow flexing in one direction easier than others. For example, the bottom portion of the coupling member can be softer than the top portion of the coupling member such that the frame is biased to bend downward when the interface is on a patient. Furthermore, the coupling member can advantageously help reduce the probability of the seal moving or being displaced on the user's face due to the frame being moved or pulled. The coupling member can provide the ability for the frame to have relative and independent movement from the seal.

Other configurations are possible. In some configurations, the coupling member can be attached directly to the mask seal and mask frame without male connector portions. The coupling member can be attached by any of a variety of suitable means, such as adhesives, welding, and the like. In some configurations, the coupling member can be removably attached such as with clips, hook and loop fasteners, straps, screws, and the like. In some configurations, the coupling member can be integrated into one or both of the mask frame and the mask seal. For example, the coupling member can be overmoulded onto the mask seal at one end and attached to the mask frame at the other end through any of the attachment means discussed previously.

With reference to FIG. 3, in some configurations, the mask frame 320 of the interface 300 includes a frame inlet 324 that receives the first end 332 of the elbow 330, and a frame outlet 326 that is received by a seal inlet 314 of the mask seal 310. In the illustrated configuration, the frame inlet 324 is a female connector portion and the first end 332 is a ball joint. The illustrated configuration also shows the frame outlet 326 as a male connector portion and the seal inlet 314 as a female connector portion. In other configurations, the connections can be reversed, for example the frame outlet can be a female connector portion and the seal inlet can be a male connector portion. In some configurations, the seal inlet 314 of the mask seal 310 and the frame outlet 326 of the mask frame 320 define a ball and socket configuration with a common rotational center 328. Other configurations are possible, such as rotational bearings, coiled shafts and universal joints.

Advantageously, the two couplings shown in FIG. 2 and FIG. 3 can enable independent movement between the frame and the seal which contacts the patients face. In some configurations, the independent movement is relative movement between the portion of the mask frame that is coupled to the mask seal and the portion of the mask seal that is coupled to the mask frame. In other words, the relative movement is between the two mounting locations. In some configurations, the independent movement between the frame and the seal is a slip movement. In other words, the independent movement is along a slip plane 260 defined across the mask frame of the interface, as illustrated in FIG. 2. The slip plane 260 can be generally normal to a plane that extends in a generally vertical direction and that substantially bisects the interface. In some configurations, the relative movement can include movement generally perpendicular to the slip plane. In some configurations, the relative movement is constrained to a generally spherical boundary with a common rotational center, such as that created by a ball and socket type joint. In some configurations, the relative movement can be along the principal axis of the ball and socket type joint (i.e., the axis of connection of the ball and socket). In some configurations, the relative movement is rotational and constrained to a generally cylindrical boundary, such as that created by a shaft and bearing type joint. In some configurations, the relative movement can be permitted along an axis of the cylindrical boundary. In some configurations, any combination of these relative movements can result. In some configurations, the ball and socket type joint can be asymmetric to allow flexing in one direction easier than others, or decoupling in one direction easier than others.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A patient interface, comprising:
a seal portion sized and shaped to surround a nose and/or a mouth of a user and adapted to create at least a substantial seal with the user's face, the seal portion comprising a seal inlet;
a frame portion comprising a frame inlet and a frame outlet, wherein the frame portion comprises attachment points for headgear;
a connector that permits the patient interface to be coupled to a conduit that is in fluid communication with a gas delivery device, the connector configured to be coupled with the frame inlet; and
a coupling between the seal inlet and the frame outlet to permit the seal portion to move relative to the frame portion, wherein the coupling comprises a male connector portion and a female connector portion, the male connector portion and female connector portion cooperating to form a ball and socket joint, wherein the coupling is generally the same size and generally aligned with the frame inlet, wherein the frame outlet comprises the male connector portion, and the seal inlet comprises the female connector portion.

2. The patient interface of claim 1, wherein the relative movement of the seal portion is constrained to a spherical boundary.

3. The patient interface of claim 1, wherein relative movement is permitted relative to a rotational center of the seal inlet and the frame outlet.

4. The patient interface of claim 1, wherein relative movement is permitted relative to a common rotational center of the seal portion and the frame portion.

5. The patient interface as claimed in claim 1, wherein the connector is an elbow, and a first end of the elbow is a ball and the frame inlet is a female connector portion adapted to receive the ball.

6. The patient interface as claimed in claim 1, wherein the frame portion is rotatable with respect to the seal portion with three rotational degrees of freedom.

7. A patient interface, comprising:
a seal portion sized and shaped to surround a nose and/or a mouth of a user and adapted to create at least a substantial seal with the user's face, the seal portion comprising a seal inlet;
a frame portion comprising a frame inlet and a frame outlet, wherein the frame portion comprises attachment points for headgear;
a connector that permits the interface to be coupled to a conduit that is in fluid communication with a gas delivery device, the connector configured to be coupled with the frame inlet; and
wherein the frame outlet is a male connector portion and the seal inlet is a female connector portion, the frame outlet received in the seal inlet, to form a coupling that permits the seal portion to move relative to the frame portion, wherein the coupling is generally the same size and generally aligned with the frame inlet, wherein the seal inlet comprises a socket and the frame outlet comprises a complementary ball to form a ball and socket joint.

8. The patient interface as claimed in claim 7, wherein relative movement is permitted about a rotational center.

9. The patient interface of claim 7, wherein the relative movement of the seal portion is constrained to a spherical boundary.

10. A patient interface, comprising:
a seal portion sized and shaped to surround a nose and/or a mouth of a user and adapted to create at least a substantial seal with the user's face, the seal portion comprising a seal inlet;
a frame portion comprising a frame inlet and a frame outlet, wherein the frame portion comprises attachment points for headgear;
a connector that permits the interface to be coupled to a conduit that is in fluid communication with a gas delivery device, the connector configured to be coupled with the frame inlet; and
wherein the frame outlet is a male connector portion and the seal inlet is a female connector portion, the frame outlet received in the seal inlet, to form a coupling that permits the seal portion to move relative to the frame portion, wherein the coupling is generally the same size and generally aligned with the frame inlet, wherein the frame portion is rotatable with respect to the seal portion with three rotational degrees of freedom.

11. A patient interface, comprising:
a seal portion sized and shaped to surround a nose and/or a mouth of a user and adapted to create at least a substantial seal with the user's face, the seal portion comprising a seal inlet;
a frame portion comprising a frame inlet and a frame outlet, wherein the frame portion comprises attachment points for headgear;
a connector that permits the interface to be coupled to a conduit that is in fluid communication with a gas delivery device, the connector configured to be coupled with the frame inlet; and
wherein the frame outlet is a male connector portion and the seal inlet is a female connector portion, the frame outlet received in the seal inlet, to form a coupling that permits the seal portion to move relative to the frame portion, wherein the coupling is generally the same size and generally aligned with the frame inlet, wherein the connector is an elbow, and a first end of the elbow is a ball and the frame inlet is a female connector portion adapted to receive the ball.

* * * * *